US006403060B1

(12) United States Patent
Bornstein et al.

(10) Patent No.: US 6,403,060 B1
(45) Date of Patent: *Jun. 11, 2002

(54) PREPARATION FOR DENTAL TREATMENT

(75) Inventors: Rolf Bornstein, Stockholm; Dan Ericson, Malmo, both of (SE)

(73) Assignee: Mediteam Dentalutveckling I, Savedalen (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,984

(22) PCT Filed: Jan. 7, 1999

(86) PCT No.: PCT/SE99/00005

§ 371 (c)(1),
(2), (4) Date: Aug. 25, 2000

(87) PCT Pub. No.: WO99/34765

PCT Pub. Date: Jul. 15, 1999

Related U.S. Application Data

(63) Continuation-in-part of application No. PCT/SE97/01887, filed on Nov. 11, 1997.

(30) Foreign Application Priority Data

Jan. 9, 1998 (SE) .............................. 9800025

(51) Int. Cl.[7] .............................. A61K 7/20; A61K 7/22
(52) U.S. Cl. ................ 424/53; 433/215.1; 424/54
(58) Field of Search ............................ 424/49, 88, 53

(56) References Cited

U.S. PATENT DOCUMENTS

| 3,903,252 A | * | 9/1975 | Stearns et al. ........... 424/49 |
| 3,998,945 A | | 12/1976 | Vit ........................... 424/53 |
| 4,271,030 A | * | 6/1981 | Brierley et al. ............ 252/98 |
| 4,561,994 A | * | 12/1985 | Rubin et al. ........ 252/187.23 |
| 4,710,217 A | | 12/1987 | Bailey et al. ............... 65/31 |
| 4,802,950 A | | 2/1989 | Croll ........................ 156/629 |
| 4,992,256 A | * | 2/1991 | Skaggs et al. ............. 424/49 |
| 5,688,756 A | * | 11/1997 | Garabedian et al. ...... 510/369 |
| 5,697,985 A | * | 12/1997 | Good et al. ................. 8/528 |
| 5,827,810 A | * | 10/1998 | Brodbeck et al. ......... 510/369 |
| 5,851,421 A | * | 12/1998 | Choy et al. .......... 252/187.26 |
| 6,017,515 A | * | 1/2000 | Van Den Bosch .......... 424/53 |
| 6,100,228 A | * | 8/2000 | Argo et al. ............... 510/379 |

FOREIGN PATENT DOCUMENTS

| EP | 0 398 893 B1 | 11/1990 |
| EP | 0 398 893 B1 | 10/1993 |
| WO | WO 89/05135 | 6/1989 |

* cited by examiner

*Primary Examiner*—Shep K. Rose
(74) *Attorney, Agent, or Firm*—Connolly Bove Lodge & Hutz

(57) ABSTRACT

The invention relates to a preparation for use in chemical-mechanical treatment of caries in the form of a two-component caries dissolving liquid in which one of the components consists of sodium hypochlorite and the other component of a substance with the ability to reduce the aggressive influence of sodium hypochlorite on mucous membranes. The other component is a gel component which consists of a gel substance without any amino acids or a gel substance mixed with one or more amino acids.

8 Claims, No Drawings

PREPARATION FOR DENTAL TREATMENT

REFERENCE TO RELATED APPLICATION

This Application is a 371 of PCT/SE99/00005, filed Jan. 7, 1999; a Continuation-in-Part of PCT/SE97/01887, filed Nov. 11, 1997, entered into the U.S. Ser. No. 09/308,163.

The present invention relates to a preparation for chemical-mechanical treatment of caries by means of a caries-dissolving liquid in which the active component consists of sodium hypochlorite.

In traditional caries treatment the attacked tooth substance is removed mechanically by means of a high-speed drill. Such a caries treatment is often a painful and unpleasant experience for the patient. Some of the patients feel so uncomfortable with the treatment that they wait far too long before they go to the dentist, which means that it is often too late to save the caries attacked teeth. Extraction of the teeth is then the only treatment method that is left.

However, there are other methods which are based on a chemical-mechanical treatment for the removal of the caries attacked tooth substance. A method of this type is described in SE 460258. According to this method a two-component liquid is mixed and then immediately applied on the caries site. Functioning in a biochemical way, the liquid makes the caries attacked substance soft without causing any damage to the tooth or the soft tissue. After 10–15 seconds the dentist can start removing the softened carious substance by scraping. The scraping operation continues until all carious substance has been removed. Then the cavity is sealed with a suitable filling material.

According to the patent the two-component liquid consists of a sodium hypochlorite component and an amino acid component. The amino acid component consists of three amino acids with different charge states in the side chain; one neutral, one with a negative net charge and one with a positive net charge.

Unlike the conventional mechanical caries treatment this biological treatment method is usually not painful at all. Neither does it require any investments in expensive equipments.

According to the treatment method the admixed two-component liquid is applied in drops on the tooth so that the entire carious formation is covered and the caries affected tissue is softened. After 10–15 seconds a mechanical removal of the softened carious substance can be initiated. The softened carious dentine (the tooth substance) is removed with the use of a scraping instrument. After some scraping the solution becomes turbid due to suspended carious substance and can be exhausted by suction or wiped away.

The above steps are repeated until the solution remains clear. In order to minimize any discomfort and the experience of pain for the patient any removal of the solution by means of a cold air stream or cold water flushing should be avoided. Instead, cotton pellets are used to remove the solution. When the carious substance has been completely removed the cavity is sealed with a suitable filling material.

For most carious formations the treatment has to be repeated in several steps until the solution remains clear. Due to the repetition of the procedure a relatively large volume of the two-component liquid is required. Since the liquid has a low viscosity as well it easily spreads itself outside the carious site and there is a risk for liquid waste on the surrounding tissue. It might be difficult and/or time-consuming for the dentist to remove such a solution which has been spread or which has been unintentionally spilt outside the carious site.

In order to facilitate the handling of such a two-component liquid it is previously known to add a viscosity increasing substance (gel substance) and a coloring agent to the liquid, see SE 96.04210-6. The gel substance should then have such properties that the aggressive influence of the sodium hypochlorite on mucous membranes is reduced, preferably it is a carboxy methyle cellulose, and the coloring agent should have the ability to interact with the carious substance. According to a preferred embodiment the coloring agent consists of Erythrosin (E 127 B).

In addition to the fact that the gel substance and the coloring agent facilitates the application of the preparation by making it more visible and viscous, they have also other advantages in connection with the removal of carious substance. During the treatment of the carious site with the additional gel substance preparation the turbidity that appears is an indication of the fact that still more carious tooth substance has to be removed. More gel substance is then applied until no more turbidity appears. This is an indication that all carious substance has been removed. The coloring agent has been introduced for indicating carious tooth substance, in the tooth itself before it has been removed, but also in the gel substance to make the turbidity more visible as the suspended particles in the solution are colored.

Even if this type of caries dissolving preparation has a very good function and is easy to handle, a specific amino acid component of the type having three amino acids, with different charge states in the side chain, as well as a gel substance and a coloring agent has been required so far and which have been mixed with the sodium hypochlorite component just before the application of the preparation.

Quite unexpectedly it has now turned out that the component to be mixed with the sodium hypochlorite component could be just a gel component in the form of a gel substance admixed or not with one or more amino acids. Specifically, it is not required that the gel component is admixed with just three amino acids according to said prior art. The gel component could be just a gel substance or it could be a gel substance mixed with one, two, four or more amino acids. However, the gel component is added to the sodium hypochlorite component immediately before the treatment, just as the previous amino acid component.

The gel substance interacts with the hypochlorite and reduces its aggressive influence on tissue. As the interaction between the gel and the tissue is happened in the gel/tissue interface, active components will be rapidly consumed in this interface zone and the undesired aggressive influence of the active components is reduced compared to a solution which is spread over a larger surface. On the carious site the gel is worked all the time and new interface zones are formed continuously with the result of an optimal carious dissolution. This also means that smaller volumes could be used and that it takes some time before the gel is consumed.

According to a preferred embodiment the gel substance consists of a methyle cellulose or any other polysacharide, preferably carboxy methyle cellulose.

Similar to the previously known two-component solution a coloring agent, with the ability to interact with carious tooth substance, has been added to the gel substance component, preferably Erythrosin (E 127 B).

In the following an example of a suitable preparation will be described more in detail.

According to the invention the preparation consists of a sodium hypochlorite component, which has a strong dissolving effect on the carious substance, and a gel component which, when mixed with the sodium hypochlorite component, interacts with hypochlorite, and give compounds containing active chlorine which, while retaining a caries-dissolving quality, does not show the aggressiveness of sodium hypochlorite towards mucous membranes. The degradation process of the gel substance starts as soon as the components have been mixed together.

The gel substance component preferably consists of a 2–10% carboxy methyl cellulose which concentration is sufficient for the gel substance alone to reduce the aggressive influence of the sodium hypochlorite on mucous membranes. The gel substance component also comprises a coloring agent of 0,04% Erythrosin (E 127 B), acid red or Xantene.

The life-time of the caries-dissolving solution is relatively short, 20–30 minutes, and it is therefore important that the solution is used immediately in order to have a good effect. In this connection the carboxy methyl cellulose has the advantage that the viscosity of the gel is dramatically reduced when the solution mixed with the sodium hypochlorite component gradually becomes inactive with respect to its caries-dissolving ability. The degradation will be clearly visible after approximately 30 minutes in room temperature as the liquid then has lost most of its viscosity. The gel substance then functions as an indicator when the solution becomes inactive for caries dissolution.

The carboxy methyl cellulose also has a lubricating effect which reduces the friction and thereby the pain for the patient in connection with mechanical scraping removal of carious tooth substance. The high pH-value solute organic material more easily which means a specific soap effect. The high pH-value also has a specific adstringend effect on the tissue which reduces the effect of possible bleedings in the soft tooth tissue.

By adding a coloring agent the liquid of course becomes more visible, for instance in case of spillage. By using a coloring agent of a type which can interact with carious tooth substance, such as Erythrosin which has the ability to interact with carious tooth substance, the suspended material will be more visible. The coloring agent in the form of Erythrosin colors carious dentine to a certain extent and has therefore the advantage of making the carious dentine material more visible.

Also other small ingredients could be added into the gel substance component. For instance EDTA (Ethylene diamine-tetra-acetic acid) and urea, which are previously known per se and used in the dental field as a cleaning substance for root surfaces and root canals, could be provided into the gel substance either separately or together in order to increase the caries dissolution effect.

The invention is not limited to the example that has been described, but can be varied within the scope of the accompanying claims. It should then be understood that it is not required but the gel substance component could be mixed with a coloring agent or other additional ingredients as described.

What is claimed is:

1. A preparation for chemical-mechanical treatment of caries in the form of a two-component caries-dissolving liquid wherein said liquid consists of:

a first component comprising sodium hypochlorite, wherein said first component is substantially free of viscosity increasing substances; and a second component comprising a viscosity increasing substance, a coloring agent adherent to suspended carious tooth substance, and amino acids; said viscosity increasing substance together with the amino acids having the ability to reduce the aggressive influence of the sodium hypochlorite on mucous membranes; and wherein said first and second components are arranged to be mixed by the dentist before the liquid is applied on the carious site to soften the caries effected tissue.

2. A preparation according to claim 1 characterized in that the gel component consists of a gel substance only.

3. A preparation according to claim 1 characterized in that the gel substance is a carboxy methyl cellulose or other polysacharide substance.

4. A preparation according to claim 1 characterized in that the gel substance comprises a coloring agent, preferably Erythrosin (E 127 B), acid red or xantene.

5. A preparation according to claim 1 characterized in that the gel component consists of 2–10% carboxy methyl cellulose and 0,04% Erythrosine.

6. A preparation according to claim 1 characterized in that EDTA and/or urea has been added to the gel component.

7. A preparation for chemical mechanical treatment of caries, according to claim 1, wherein said second component is substantially free of amino acids.

8. A preparation for chemical-mechanical treatment of caries, according to claim 1, wherein said second component comprises amino acids.

* * * * *